United States Patent [19]

Meyer

[11] Patent Number: 5,211,679
[45] Date of Patent: May 18, 1993

[54] AIR QUALITY MONITORING METHOD AND APPARATUS

[76] Inventor: Raymond A. Meyer, 1021 Calle Las Trancas, Thousand Oaks, Calif. 91360

[21] Appl. No.: 715,112

[22] Filed: Apr. 25, 1991

[51] Int. Cl.⁵ .............................................. G01N 1/00
[52] U.S. Cl. ................................................ 73/863.12
[58] Field of Search ...................... 73/1 R, 170 R, 171, 73/863.01, 863.11, 863.12, 863.21, 864.31, p864.41, 864.81, 864.91

[56] References Cited

U.S. PATENT DOCUMENTS

| | | | |
|---|---|---|---|
| 2,307,602 | 1/1943 | Penney et al. | 73/863.21 |
| 2,687,185 | 8/1954 | McChesney | 73/863.12 |
| 4,398,412 | 8/1983 | Huneidi | 73/170 R |
| 4,488,887 | 12/1984 | Angel et al. | 73/863.12 |
| 4,638,674 | 1/1987 | Redmann | 73/863.12 |
| 4,665,743 | 5/1987 | Masniere et al. | 73/170 R |
| 4,697,462 | 10/1987 | Daube, Jr. et al. | 73/170 R |
| 4,713,618 | 12/1987 | Carlson et al. | 73/1 R |
| 4,732,046 | 3/1988 | Lawrence et al. | 73/863.12 |

FOREIGN PATENT DOCUMENTS

| | | | |
|---|---|---|---|
| 0143479 | 11/1980 | Japan | 73/171 |
| 0779965 | 11/1980 | U.S.S.R. | 73/171 |
| 1045004 | 10/1966 | United Kingdom | 73/863.12 |

OTHER PUBLICATIONS

Dalmon et al., "The Cerl Deposition Sampler", Bulletin No. 297, Central Electricity Gen. Board, London, Apr. 1978.

Primary Examiner—Robert Raevis

[57] ABSTRACT

A method for studying and evaluating the extent and type of air pollution by evaluating samples collected from the earth's atmosphere including the steps of providing cyclic, computer controlled, condensation on a chilled surface where the collection form is either frost or solid depending upon collection conditions and the frost or solid is subsequently converted to liquid form for evaluation and testing.

2 Claims, 1 Drawing Sheet

AIR QUALITY MONITORING METHOD AND APPARATUS

BACKGROUND

1. Field of Invention

This invention relates to the determination of air quality as related to acidic precipitation and/or condensation.

2. Present State of the Art

A phenomena called Acid Rain is damaging our ecological system. It is of great concern to the world's population. Acid rain is normally described as pollution that is washed from the air and deposited, along with the rainfall, upon the earth. Within the scientific community, acidity is measured and reported as pH. pH is defined as the negative logarithm of the hydrogen ion concentration. pH values range between 1 and 14. A pH of 1 is very acid, 7 is neutral and 14 is very caustic. Typical reported values for acid rain are in the 3.5 to 5 pH range. The National Bureau of Standards supplies reference material #2694 in pH of 4.30 and 3.59. Neutral pH 7 is not reached in normal rainfall due to carbonic acid generated by solution of carbon dioxide. Typical values for uncontaminated rainfall are in the 5.5 to 5.6 pH range. The acidic solutions have been shown to have a deleterious effect on all facets of mankind. These include lakes, streams, trees, vegetation and other facets of nature. Buildings, historic sites, exposed works of art etc are also suffering serious surface damage.

The acidity of precipitation is typically determined by collecting discrete samples of rainfall and measuring the pH with an appropriate electrode. In most studies bulk samples taken during a complete rainfall event are evaluated. The first portion of a rainfall event contains the bulk of the acidic components. Later rain falls through scrubbed air and is less acid. This follow-on rainfall greatly dilutes the acidity of the sample. These data serve well in evaluating damage to lakes and streams. Due to the great dilution, the value of the data in predicting damage to surfaces is of limited value. The collected rainfall samples are typically transferred to a distant laboratory for analysis. These samples change with time unless stringent measures such as preservative addition and cold storage are employed to maintain their integrity. The attendance of an operator is required after or during each rainfall event.

As the rain falls through the air, it not only scrubs the atmosphere of it's acidic components but also it's atmospheric dust. In many locations, this dust is quite basic. It reacts with the acid and partially neutralizes it. While this is not a factor in the study of the gross effects of acid rain, it reduces the value of the data for air quality management. It would be far better for the investigator to have the option of eliminating the effect of the atmospheric dust.

Rainfall events are relatively rare in the polluted world. This precludes continual monitoring of the acidic pollution of the atmosphere.

BRIEF DESCRIPTION OF THE DRAWING

The only FIGURE is the system as described in the written specification.

INVENTION THEORY

Figure 1:
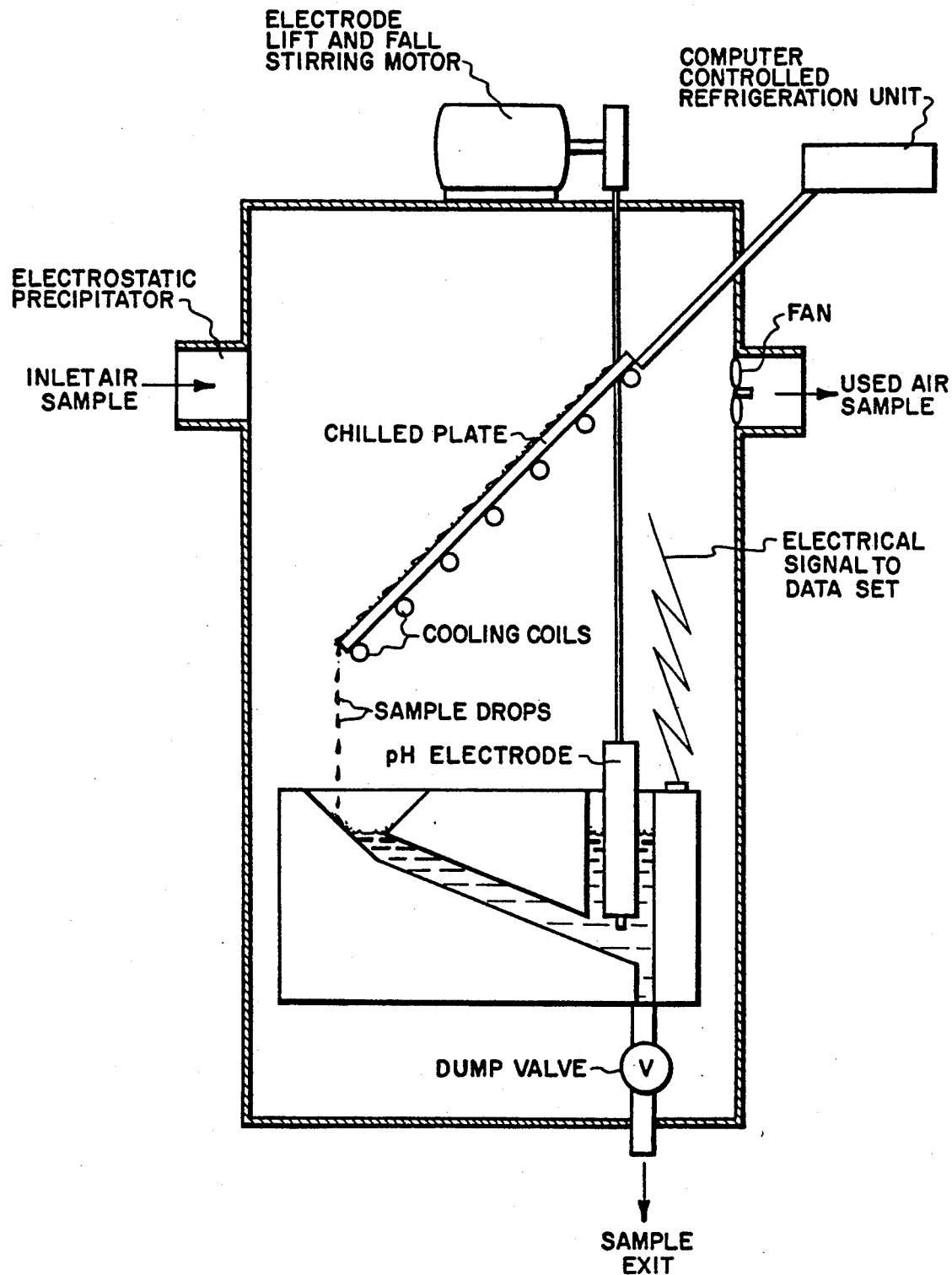

It is the contention of this invention that acid rain is not the major contributor to the damage of exposed surfaces. The acidic components are quite dilute and are washed from the surfaces by low acid follow-on rainfall.

Acidic condensation, the subject of this invention is proposed as the major culprit in generation of surface damage. Consider that when water is condensed from the atmosphere as dew or fog, it contains the same acidic components that are in acid rain. There is no follow-on low-acid rainfall to wash the surface clear of the strong acid. Rather, the water evaporates and leaves behind sub-microscopic dots of concentrated acid. This acid never evaporates and stays in contact to react with the surface.

AN ACID CONDENSATION MONITORING METHOD

The pH of dew in several urban locations was measured and found to be in the acidic 3-4 range substantiating the theory that the dew contains the same acidic constituents as acid rain. Dew samples taken in remote, semi-pristine locations had much higher pH. This indicates a lower acidity. Rainfall and even dew-fall events are relatively rare in many parts of the polluted world. The ecologist cannot monitor the cause or source of acid rain causing pollutants on a regular basis. Another method for collecting the water from the atmosphere was invented. This method takes the form of exposing the atmosphere to a chilled collector plate whereupon the water is removed and typically collects as frost. The frost was then caused to melt and the collected sample allowed to flow into or through a pH measurement cell. In one embodiment, a thermostated heater was used to assure melting of the frost in the allotted time. Reverse cycle defrosting wherein the flow of the refrigerant was reversed was used to promote melting in another embodiment. A typical cycle was 105 minutes with the compressor on to collect frost and 15 minutes off or with reversed refrigerant flow to allow the frost to melt and flow into the pH measurement cell. In the case of extremely dry air, the condensation cycle may be extended as required to allow collection of sufficient sample.

The rate of sample collection slows when the chilled collector plate is covered with frost. This is due to the relatively low thermal conductivity of ice and frost. In one embodiment, the collector was fitted with a scraper to collect the frost as it was formed. Although the sample collection rate increased, it was deemed unnecessary to include this feature except in extremely dry atmospheric conditions.

As atmospheric dust is normally basic, it reacts with the acid of the collected liquid sample and partly neutralizes it. This is the case of the present art where it is impossible to eliminate the effect of atmospheric particulates. A preferred embodiment of the system includes an electrostatic dust precipitator in the air flow prior to the chilled collection plate. This type of dust removal device does not affect the sample as air filters could. Additionally the chosen type removes particulate material down to 0.01 micron in size. The investigator has the option of turning off the voltage to the precipitator should he desire a study including the effect of atmospheric particulates.

The apparatus was under complete computer control and operated in an unattended-self calibrating mode until data transfer to a central office for off-site reduction was required.

One embodiment of the invention included a means for collecting and storing individual samples. The samples were then transferred to a laboratory for detailed analysis. Proper means of limiting sample degradation during storage and transfer such as preservative addition and cold storage were employed.

The computer program that controls the various actions of the system is not a part of the invention. In one embodiment, it was written in the common Basic language and used with a Commodore 64 C computer. Any suitable computer can be programmed to generate the desired commands by a person skilled in the art.

It is very difficult to accurately determine the pH of low-ionic solutions (containing minute amounts of chemicals other than water). One manufacturer distributes a special "pure water" pH test kit. The kit includes an ionic adjustor to increase the ionic strength without altering the pH. The use of an integral measurement cell in this apparatus allows the addition of such adjustors should they be deemed of value by the investigator. The adjustor was added to the cell immediately following the dump cycle that emptied the cell of the previous sample. The flow of the next sample and the mixing action of the electrode distributed the adjustor within the sample.

Automatic calibration under computer control was performed once a day by causing the cell to be filled with diluted pH 4 buffer followed by diluted pH 7 buffer. Cross contamination between buffers was not a problem but strenuous efforts in cell design as described in the following paragraph and washing after calibration were required to eliminate contamination of the subsequent condensation samples. The investigator is cautioned to test his embodiment for cross-contamination.

Although not included in the invention, complete disclosure dictates that salient parts of cell design be included. The cell cannot contain any void space exposed to the sample stream which could trap calibration buffer. This could typically be the small clearance between the electrode and the wall of the cell. Even amounts in the sub-microliter range can mix with subsequent samples to invalidate data. Consider that buffer standards are selected to resist change by dilution. In one embodiment, the cell was constructed of solution welded plastic with all voids filled with the cement. Stirring of the sample may be achieved with the common magnetic stirrer bar. In an effort to reduce sample volume requirements, one embodiment stirred the cell by alternately raising and lowering the electrode. A 2 mm transition at 120 cycles proved satisfactory. Other techniques could be equally suitable.

During the automatic calibration cycle, the voltages generated when the electrode was in the pH 4 and in the pH 7 standards were entered into the computer data to allow off-site correction of the raw measurement values during data processing.

Sample pH which is converted to a voltage by the pH electrode was stored in computer memory until the data was transferred to a central point for off-site data reduction. Many means of data transfer were tested and used. These include magnetic media exchange such as disk and tape, EEPROM (electric erasable programable read only memory) chip exchange, telephone line transfer and even printed records. It was deemed possible but infeasible to process the data on-site. The selection of the optimum data transfer method is left to the skilled operator.

Provision was made for a rainfall sensor to interrupt the frost collection cycle and deploy a rainfall collector during rainfall events. The design of the collector can follow the practice of the several commercial units. In this mode the system acts as an automated, continuous, rainfall collector and measurer, and pH evaluator. When the rainfall ceased, the system reverted to the normal frost-collection mode.

CONCLUSION, RAMIFICATIONS AND SCOPE OF INVENTION

The invention consists of a method for continual cyclic evaluation of air quality as related to acid deposition. Several possible embodiments are suggested to perform such evaluation. The preferred embodiment overcomes many of the faults of the present art such as dependence upon rainfall events to obtain samples, infrequent batch type sampling, sample reaction with atmospheric particulates, frequent operator attention and others. The basic concept corrects a serious misconception in the relation between acid precipitation and surface damage.

The preferred embodiment consists of a chamber containing a refrigeration cooled collector plate. The access of the atmosphere to the chamber is through an electrostatic precipitator allowing the investigator the option of removing atmospheric particulates before collecting the sample. The system operates under complete, unattended, computer control of all functions. The computer program includes an auto-calibration routine that successively fills the analysis cell with pH 4 and pH 7 buffers as often as the investigator desires. Data are stored in computer memory until transfer to a central processing point is required. The system operates in a cyclic mode during non-rainfall event periods and switches to an automated pH determination mode during rainfall. The timing of a typical two hour cycle is shown in table 1. When dryness of the air dictates, the collection portion of the cycle may be extended.

TABLE 1

| TIME | ACTION |
|---|---|
| 0:00:00 | refrigerator on |
| 1:45:00 | refrigerator off |
| 1:45:00 | cell dump valve opened |
| 1:45:30 | cell dump valve closed |
| 1:45:31 | condenser plate heater thermostat on |
| 1:45:31 | electrode transition action stirring started |
| 1:45:31 | pH electrode data acquisition and storing started |
| 1:59:59 | all actions stopped and cycle restarted |

While my above description contains many specifities, these should not be construed as limitations to the scope of the invention, but rather as exemplification of some embodiments thereof. Accordingly, the scope of the invention should be determined not by the embodiments described but rather by the appended claims and their legal equivalents.

What is claimed is:

1. A method for studying and evaluating the extent and type of air pollution by evaluating samples collected from the earth's atmosphere including the steps of providing cyclic, computer controlled, condensation on a chilled surface where the collection form is either frost or solid depending upon collection conditions and the frost or solid form is subsequently converted to liquid form for evaluation and testing.

2. The method of claim 1 further including the step of providing a means of excluding the effect of atmospheric particulates upon the samples to facilitate evaluation of pollution sources prior to sample reaction with atmospheric particulates.

* * * * *